(12) United States Patent
Bunodiere et al.

(10) Patent No.: US 7,445,614 B2
(45) Date of Patent: Nov. 4, 2008

(54) SUBCUTANEOUSLY IMPLANTABLE ACCESS PORT

(75) Inventors: Michel Bunodiere, Neuilly-sur-Seine (FR); Guy Nadal, Poitiers (FR)

(73) Assignee: B. Braun Medical SAS, Boulogne (FR)

( * ) Notice: Subject to any disclaimer, the term of this patent is extended or adjusted under 35 U.S.C. 154(b) by 601 days.

(21) Appl. No.: 10/692,727

(22) Filed: Oct. 27, 2003

(65) Prior Publication Data

US 2005/0075614 A1 Apr. 7, 2005

(30) Foreign Application Priority Data

Oct. 25, 2002 (FR) .................................. 02 13386

(51) Int. Cl.
*A61M 31/00* (2006.01)
(52) U.S. Cl. .............................. 604/288.02; 604/288.04
(58) Field of Classification Search ................ 604/284, 604/533, 288.01–288.04, 890.1, 891.1
See application file for complete search history.

(56) References Cited

U.S. PATENT DOCUMENTS

| | | | |
|---|---|---|---|
| 4,718,894 A | * | 1/1988 | Lazorthes .............. 604/288.02 |
| 5,084,015 A | * | 1/1992 | Moriuchi ............... 604/288.02 |
| 5,328,465 A | | 7/1994 | Kratoska et al. |
| 5,466,218 A | | 11/1995 | Srisathapat et al. |
| 5,527,307 A | * | 6/1996 | Srisathapat et al. ...... 604/892.1 |
| 6,287,293 B1 | | 9/2001 | Jones et al. |
| 6,527,754 B1 | * | 3/2003 | Tallarida et al. ........ 604/288.04 |

FOREIGN PATENT DOCUMENTS

| | | |
|---|---|---|
| AT | 391 813 B | 12/1990 |
| DE | 197 45 654 A1 | 4/1999 |
| WO | 02/083208 A2 | 10/2002 |

* cited by examiner

*Primary Examiner*—Matthew F Desanto
(74) *Attorney, Agent, or Firm*—Young & Thompson

(57) ABSTRACT

A chamber for the infusion of a medicament. The chamber includes a reservoir, an outer casing having a base wall and a lateral wall, a region for access to the reservoir, and a duct for the diffusion of the medicament. A contour of the base wall is substantially triangular. The casing has a shape tapered in a first direction, and a terminal portion of the diffusion duct extends tranversely, and preferably perpendicularly, to the direction of tapering.

7 Claims, 2 Drawing Sheets

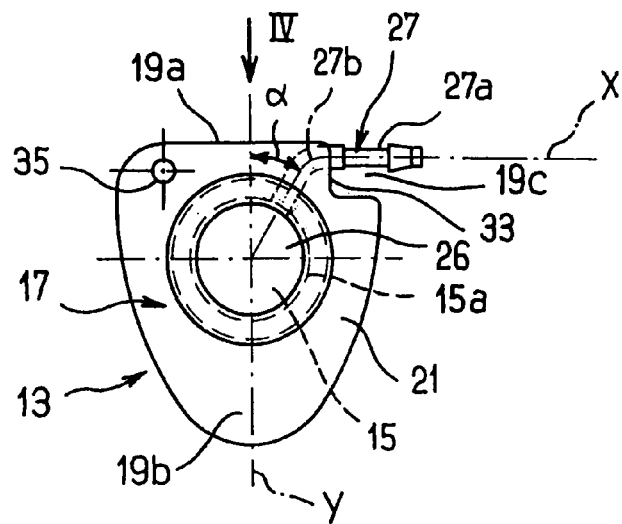
FIG_3
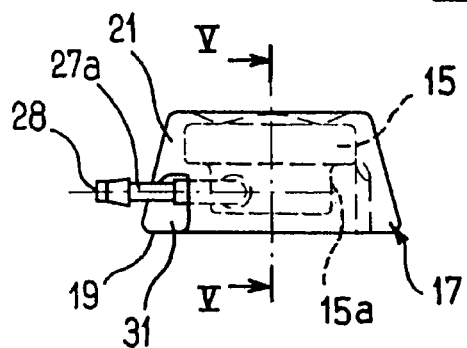
FIG_4
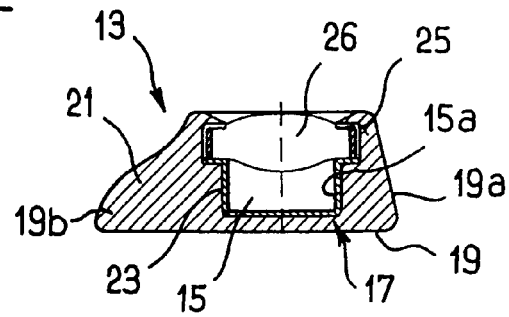
FIG_5
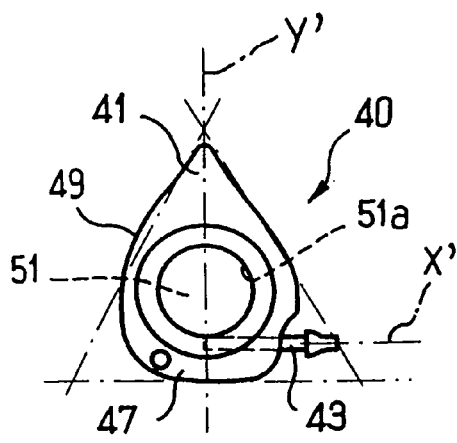
FIG_6
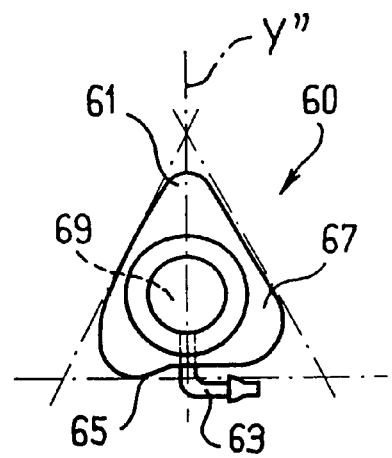
FIG_7

SUBCUTANEOUSLY IMPLANTABLE ACCESS PORT

BACKGROUND OF THE INVENTION

The invention relates to an implantable chamber for the infusion of a medicament, which chamber is to be implanted subcutaneously by way of an incision in a body.

Such chambers are already known; they comprise a medicament reservoir, a region for access to the reservoir, which region is accessible from outside the body and which is to enable the medicament reservoir to be filled, and a diffusion duct connected to the reservoir and extending outside the latter.

Such chambers may also be used in the opposite manner, that is to say, for taking a sample of body fluid (blood in particular), the fluid collecting in the chamber from which it can be removed. Such chambers also fall within the ambit of the invention but the invention will be described hereinafter purely with reference to a chamber for the infusion of a medicament without limiting the scope of the invention to infusion chambers only.

The chamber is to be implanted beneath the skin of a patient. In the course of such an operation, the surgeon makes an incision in the dermis, for example at the thorax, and inserts an implantable chamber entirely beneath the skin. During the operation, the end of an outlet duct from the chamber is accessible at the incision for the connection of a catheter which closes the infusion site, for example the jugular vein.

After implantation, a syringe, which is introduced via the access region, may be used as a source of medicament which has to be diffused progressively in the body, or for taking a sample.

Document U.S. Pat. No. 5,951,512 describes an implantable chamber which is to transfer a liquid transdermally between a reservoir and a diffusion region inside the body of a patient. It comprises a circular medicament reservoir, a support cheek surrounding the base of the reservoir, a region for access to the reservoir, which region is located towards the top of the reservoir, is accessible from outside the device and is to enable the medicament reservoir to be filled, and a diffusion duct which is connected to the reservoir and which extends radially or tangentially towards the outside of the latter.

Document DE-197 45 654 also describes an implantable chamber having a circular medicament reservoir and a support plate surrounding the reservoir, a diffusion duct connected to the reservoir extending radially towards the outside of the latter.

Documents U.S. Pat. No. 5,328,465, WO 02/083208, EP-678 302 and AT-391 813 describe medicament pumps and not implantable chambers. They all comprise a cylindrical or lenticular body having a circular cross-section, from which extends a diffusion duct which forms a bend such that the diffusion duct has a direction substantially tangent to the reservoir.

Accordingly, an implantable chamber for the infusion of a medicament is already known, which chamber is to be implanted subcutaneously by way of an incision in a body and which comprises a medicament reservoir, a region for access to the reservoir, which region is located at a vertex of the reservoir, is accessible from outside the body and is to enable the medicament reservoir to be filled, and a diffusion duct which is connected to the reservoir and which extends outside the latter, the diffusion duct having an external terminal portion.

Such a chamber poses the following problems. Since an incision has to be made in order to put it in place, the chamber is traumatising and it is desirable to reduce that traumatism as much as possible. The chamber constitutes a foreign body which causes some discomfort which depends in particular on its volume and its shape and also on how securely it is fastened beneath the skin. Finally, another important factor is the ease with which it can be put in place by the surgeon because the longer the intervention the greater the traumatism.

SUMMARY OF THE INVENTION

The invention enables those problems to be solved by a combination of a profiled shape, which makes it difficult for the chamber to rotate on itself, and an outlet duct having an orientation such that the connection of the catheter to the duct is effected readily and rapidly while at the same time reducing traumatism.

To be more precise, according to the invention those results are obtained by the following combination of features:
- the chamber comprises an outer casing surrounding the reservoir and having a base wall and an outer lateral wall extending from the base wall to the top of the reservoir,
- the contour of the base wall is substantially triangular and such that the casing has a shape tapered towards a vertex of the triangle,
- the portion of the diffusion duct closest to the reservoir is surrounded by the casing, and
- the terminal portion of the diffusion duct, which portion is located outside the casing, extends in a direction substantially parallel with the side of the triangle opposite the tapered vertex.

Preferably, the casing also has a shape tapered towards the vertex of the triangle, in the direction of the thickness, that is to say, perpendicularly to the base wall.

Thus, advantage is taken of the synergy between the tapered outer shape, which promotes subcutaneous positioning in as small a housing as possible beneath the skin, and a diffusion duct outlet which is oriented in the direction of the incision and which enables a catheter to be connected with minimum traumatism.

The diffusion duct is located in a region of the chamber opposite the tapered end of the casing, so that this tapered portion penetrates to the base of the subcutaneous housing, and the diffusion duct is then located in the immediate vicinity of the incision made by the practitioner in the patient's skin. The connection of the terminal portion of the diffusion duct to the catheter which is to inject the product further into the body is easy and rapid and the practitioner can also readily close the incision once the chamber is in place beneath the skin.

Preferably, the reservoir has a substantially circular cross-section parallel with the base wall of the casing.

In one embodiment, the portion of the diffusion duct closest to the reservoir is radial relative to the circular wall of the reservoir, so that the diffusion duct comprises a bend between its portion closest to the reservoir and its terminal portion. Preferably, the bend in the diffusion duct is inside the casing. It is then advantageous if the bend forms an angle of approximately from 100 to 150°.

Those features simplify the manufacturing conditions of the chamber. In order to reduce the volume of the chamber and in order to ensure that the line of the cutaneous incision and the direction of the terminal portion of the diffusion duct are substantially parallel with one another, the bend in the diffusion duct is located in the casing but outside the reservoir.

In addition, those features facilitate the production of the chamber, reducing the risk of leakage at the connection between the various parts.

In another embodiment, the portion of the diffusion duct closest to the reservoir is substantially tangent to the circular wall of the reservoir.

Another aspect of the invention concerns the space requirement of the device as a whole, especially at the site of the diffusion duct outlet.

In order to reduce the space requirement of the chamber and thus to increase patient comfort, it is advantageous if the casing forms a recess at a corner of its triangular contour, and if the terminal portion of the diffusion duct opens out from the casing at the site of the recess.

Owing to its triangular shape, the implantable chamber does not tend to rotate on itself nor to migrate beneath the skin. However, some practitioners wish to fasten the chamber by suture. In that case, the chamber is advantageously such that the casing has an opening which extends through the base wall in the vicinity of the side of the triangle opposite the tapered vertex, the opening being intended for the passage of a suture thread.

BRIEF DESCRIPTION OF THE DRAWINGS

Other features and advantages of the invention will emerge more clearly from the following description of embodiments, which is given with reference to the appended drawings in which:

FIG. 3 is a plan view of a chamber according to a first embodiment of the invention;

FIG. 4 is a view in lateral elevation in the direction of arrow IV in FIG. 3;

FIG. 5 is a section according to the line V-V in FIG. 4; and

FIGS. 6 and 7 represent two other variants in plan view.

DETAILED DESCRIPTION OF THE PREFERRED EMBODIMENTS

Figure 1:
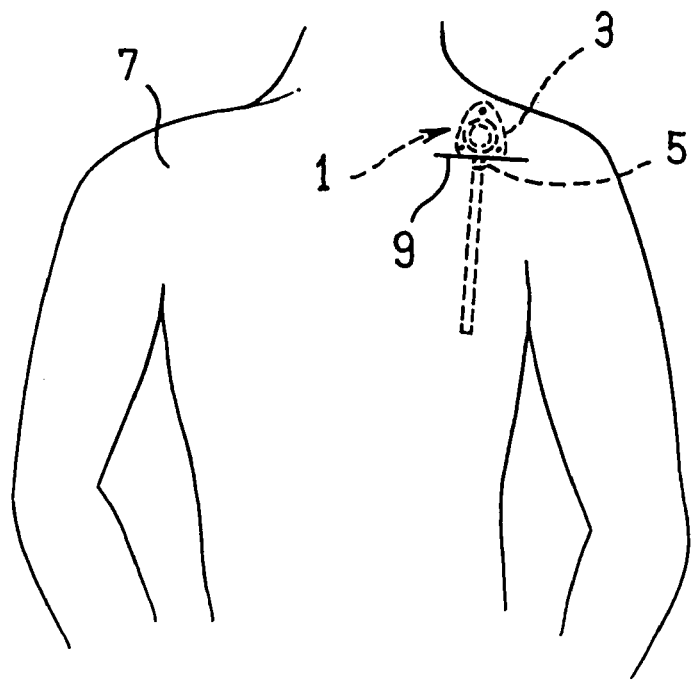
FIG. 1 illustrates the implantation of a traditional medicament infusion chamber, which is implanted subcutaneously, in the body of a patient, by way of a horizontal incision.

FIG. 1 illustrates the implantation of a traditional medicament infusion chamber 1, which is implanted subcutaneously, in the body 7 of a patient, by way of a horizontal incision. The chamber comprises a body 3 having a medicament reservoir. A diffusion (or sampling) duct 5 extends radially out of the body 3. The duct 5 is substantially perpendicular to the body in the vicinity of the horizontal incision 9 which has been made at least in the dermis of the body 7 in order to implant the chamber subcutaneously.

Figure 2:
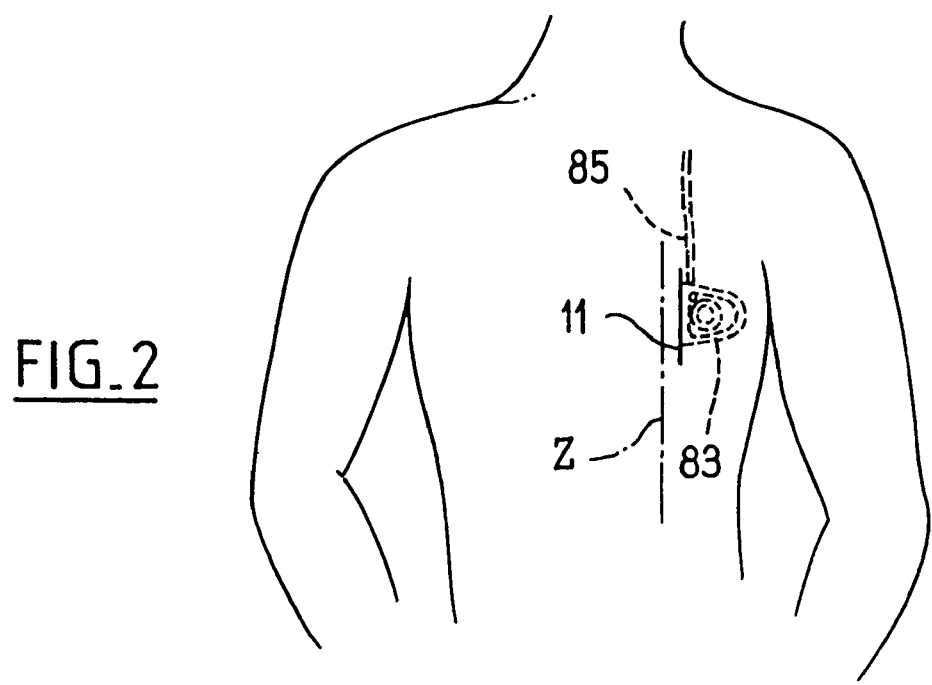
FIG. 2 illustrates the implantation of a device according to the invention by way of a vertical incision.

FIG. 2 illustrates the implantation of a medicament infusion chamber, which is implanted subcutaneously, in the body of a patient, by way of an incision 11 having a vertical direction Z. The chamber comprises a diffusion (or sampling) duct 85 which extends tangentially out of the body. The duct 85 is substantially parallel with the incision 11 which has been made at least in the dermis of the body in order to implant the chamber subcutaneously.

In FIGS. 3 to 5, an implantable chamber 13 according to the invention comprises a reservoir 15 for liquid which is surrounded by a moulded outer casing 17. The casing has a flat base wall 19 for supporting the chamber on the patient's flesh, and an outer lateral wall 21.

The reservoir 15 is advantageously composed of metal and comprises a lower dish 23 and an annular upper cap 25.

The reservoir shown has a circular cross-section, parallel with the base wall 19.

An access region formed by a membrane 26 which is both perforable and self-sealable is located above the dish 23. An annular cap 25 holds the membrane 26 between itself and the dish tightly and in a manner sealed with respect to fluids.

A metal diffusion duct 27 communicates with the reservoir. It extends radially through the circular wall 15a of the reservoir and then passes into the casing 17.

In the embodiment under consideration, the duct 27 extends in a horizontal plane parallel with the base wall 19.

The base of the casing 17 represented in FIGS. 3 to 5 is substantially triangular, with a front side 19a and a rear corner or vertex 19b in the direction of which the lateral wall is tapered, in the portion of the chamber that is to penetrate most deeply into the subcutaneous housing. It will be noted in particular in FIG. 5 that the casing 17 also has a shape which is tapered in the direction of the thickness, perpendicularly to the base wall.

In the region close to the incision, the duct 27 extends in the immediate vicinity of the front side 19a. It extends through the wall 21 of the casing near the front right corner 19c (top right in FIG. 3) and its terminal portion 27a (which extends outside the casing and terminates at the free end 28) is directed substantially parallel with the front side 19a of the base.

It will also be appreciated that the direction X of the terminal portion 27a is transverse (here perpendicular) to the axis Y which passes via the centre of the front side 19a and via the tip 19b, that is to say, which defines the direction of tapering of the casing. The duct 27 is accordingly bent. In the Figures, it has a single bend 27b located inside the covering region of the casing, outside the reservoir. It is connected to the reservoir advantageously obliquely relative to the axis Y, on the side where the outlet corner is located, in order to reduce the angle and the number of bends.

The duct preferably delimits with the axis Y an angle a of approximately from 10 to 60°, preferably from 25° to 35°. Accordingly, the bend forms an angle of from 100 to 150°, preferably from 115 to 125°.

In order to limit the overall space requirement, the corner where the duct exits has a recess 31. Accordingly, the duct 27 extends through the lateral wall 21 at the site of one of the faces 33 of that recess.

At the opposite corner of the front side (top left in FIG. 3), an opening 35 enables the practitioner to suture (more generally connect) the implantable chamber to the patient's flesh. Preferably, the implantable chamber is fastened to the body by way of this single opening. However, bearing in mind the triangular shape of the casing which enables the chamber to be held securely, such a suture is generally unnecessary.

It will be appreciated that the side where the duct 27 exits may be "towards the right" (as in FIG. 3) or, equally well, "towards the left" (solution not illustrated).

In the variant of FIG. 6, the implantable chamber 40 is in the shape of a triangle, the vertices of the front side of which are very rounded, giving a substantially "water droplet" shape. This reduction of the front side is advantageous at some implantation sites where the incision has to be particularly short.

The general direction X' of exit of the diffusion duct 43 is transverse (perpendicular in the case in point) to the general direction Y' of tapering which passes via the rear vertex 41 and via the middle of the front side 47 of the base wall 49 of this implantable chamber.

In this embodiment, the diffusion duct 43 is substantially rectilinear (or optionally very slightly curved) and is connected to the reservoir 51 substantially tangentially to the outer wall 51a of the latter. This embodiment is less advantageous than that described with reference to FIGS. 3 to 5 because it is more difficult to connect the duct to the reservoir without the possibility of leakage.

FIG. 7 represents another variant having a shape which is tapered towards the rear (region 61) and which is substantially triangular.

In this case, the implantable chamber 60 has its connecting duct 63 at the centre of the front side 65. The connecting duct is bent outside the casing 67 and is connected to the inner reservoir 69, radially to its wall, substantially on the axis of the general direction Y" of tapering which passes via the rear tip 61 and via the centre of the front side of the base. The bend is substantially at 90° relative to the axis Y". This embodiment is less advantageous than that of FIGS. 3 to 5 because the bend is not surrounded by the casing and may therefore be subjected to pivoting forces acting directly on its fasteninq to the reservoir.

The positioning of an implantable chamber according to the invention may be carried out as follows and as illustrated in FIG. 2.

First of all, the practitioner has an implantable chamber which tapers towards the rear and which therefore has, towards its front edge, a lateral outlet for the duct which connects the chamber to the diffusion catheter.

The practitioner then makes a cutaneous incision 11, for example in the patient's chest, or in the sub-clavian region. The incision is advantageously inclined relative to the horizontal and is, in particular, vertical, as indicated in FIG. 2. Such an orientation of the incision in some cases enables it to be better concealed, the scar being less visible, and sometimes permits accelerated healing.

Beyond the incision, the practitioner arranges a housing 83 in the patient's flesh, just beneath the skin. Bearing in mind the tapered shape of the implantable chamber, he may shape the base of the housing 83 into a slight point.

The practitioner then slides the implantable chamber into the housing, having taken care to select an implantable chamber whose outlet opening for the connecting duct is directed, as the case may be, either towards the top of the patient's body, as indicated in FIG. 2, or downwards (sub-clavian implantation).

Beforehand, the surgeon has slid the catheter 85 into the patient's body using an appropriate introduction/expansion device. Thus, the catheter has been slid into a vessel, for example for the distribution of a liquid cancer medicament.

One end of the catheter then extends out of the patient's body at the site of the subcutaneous housing 83 or in the immediate vicinity thereof.

The practitioner then determines the lengthwise of the catheter and connects its end to the end portion of the diffusion duct of the implantable chamber.

The terminal portion of the diffusion duct, and the adjacent portion of the catheter are then substantially parallel with the direction Z of the incision 11 and in the immediate vicinity thereof. This facilitates the manipulation by the practitioner both of the emergent portion of the catheter and of the implantable chamber.

The practitioner then fastens the implantable chamber to the patient's body, for example by suturing the front opening (such as 35 in FIG. 3). A single fastening opening on the opposite side from the catheter prevents the implantable chamber from pivoting in its housing 83.

The surgeon then re-closes the skin at the site of the incision, by suture.

The implantable chamber equipped with its catheter is then in the position and at the site indicated in FIG. 2, with the access region just beneath the skin, and therefore accessible to an appropriate needle connected to a medicament reservoir. The practitioner may also remove blood by way of the chamber reservoir.

The invention claimed is:

1. An implantable chamber for the infusion of a medicament, said chamber is to be implanted subcutaneously by way of longitudinal incision in a body, said chamber comprises:
   a medicament reservoir,
   a region for access to the reservoir, said region is located at a vertex of the reservoir, is accessible from outside the body and is to enable the medicament reservoir to be filled;
   a diffusion duct which is connected to the reservoir and which extends outside said reservoir, the diffusion duct having an external terminal portion; and
   an outer casing surrounding the reservoir and having a base wall and an outer lateral wall extending from the base wall to a top of the reservoir,
   wherein a contour of the base wall is substantially triangular and is such that the outer casing has a shape tapered towards a vertex of the triangle,
   wherein a portion of the diffusion duct closest to the reservoir is surrounded by the casing and is radial relative to a wall of the reservoir, so that the diffusion duct comprises a bend between the portion closest to the reservoir and the terminal portion, the bend of the diffusion duct being inside the casing, and
   wherein the terminal portion of the diffusion duct is located outside the casing and extends in a direction substantially parallel with a side of the triangle opposite the tapered vertex so that the terminal portion and an adjacent portion of a catheter to be connected to the terminal portion are substantially parallel with a direction of incision made for implanting the chamber.

2. The chamber according to claim 1, wherein the casing also has a shape tapered towards the tapered vertex of the triangle in a direction of thickness perpendicular to the base wall.

3. The chamber according to claim 2, wherein the reservoir has a substantially circular cross-section in a direction parallel with the base wall of the casing.

4. The chamber according to claim 2, wherein the casing forms a recess at a corner of its triangular contour, and the terminal portion of the diffusion duct opens out from the casing at the site of the recess.

5. The chamber according to claim 2, wherein the casing has an opening which extends through the base wall in the vicinity of the side of the triangle opposite the tapered vertex, the opening being intended for the passage of a suture thread.

6. The chamber according to claim 1, wherein the bend forms an angle of approximately from 100 to 150°.

7. An implantable chamber for the infusion of a medicament, said chamber is to be implanted subcutaneously by way of longitudinal incision in a body, said chamber comprises:
   a medicament reservoir having a circular wall,
   a region for access to the reservoir, said region is located at a vertex of the reservoir, is accessible from outside the body and is to enable the medicament reservoir to be filled;

a diffusion duct which is connected to the reservoir and which extends outside said reservoir, the diffusion duct having an external terminal portion; and an outer casing surrounding the reservoir and having a base wall and an outer lateral wall extending from the base wall to a top of the reservoir, wherein a contour of the base wall is substantially triangular and is such that the outer casing has a shape tapered towards a vertex of the triangle, wherein a portion of the diffusion duct closest to the reservoir is surrounded by the casing, wherein the terminal portion of the diffusion duct is located outside the casing and extends in a direction substantially parallel with a side of the triangle opposite the tapered vertex so that the terminal portion and an adjacent portion of a catheter to be connected to the terminal portion are substantially parallel, and wherein the portion of the diffusion duct closest to the reservoir is substantially tangent to the circular wall of the reservoir.

* * * * *